(12) United States Patent
Ives

(10) Patent No.: US 6,454,748 B1
(45) Date of Patent: Sep. 24, 2002

(54) DIAPER WITH A POCKET

(76) Inventor: Shari Ives, Box 6, Site 9, R.R. 2, Okotoks Alberta (CA), TOL-1TO ( * ) Notice: Subject to any disclaimer, the term of this patent is extended or adjusted under 35 U.S.C. 154(b) by 0 days.

(21) Appl. No.: 09/251,656

(22) Filed: Feb. 17, 1999

(51) Int. Cl.[7] .......................... A61F 13/15; A61F 13/20
(52) U.S. Cl. ............................ 604/385.06; 604/385.13
(58) Field of Search ..................... 604/385.1, 385.06, 604/385.13; 206/438–440

(56) References Cited

U.S. PATENT DOCUMENTS

| | | | |
|---|---|---|---|
| 3,369,545 A | * 2/1968 | Wanberg | 604/385.1 |
| 3,731,684 A | * 5/1973 | Schaar | |
| 4,085,753 A | * 4/1978 | Cellert | 604/385.1 |
| 4,430,087 A | * 2/1984 | Azpiri | 604/385.1 |
| 4,493,713 A | * 1/1985 | Izzo | 604/385.1 |
| 4,581,027 A | * 4/1986 | Alvarado | 604/385.1 |
| 4,808,175 A | * 2/1989 | Hansen | |
| 4,923,455 A | * 5/1990 | Dean et al. | 604/385.1 |
| 4,968,311 A | * 11/1990 | Chickering et al. | 604/385.1 |
| 5,071,414 A | * 12/1991 | Elliott | 604/385.1 |
| 5,304,158 A | * 4/1994 | Webb | 604/385.1 |
| 5,778,110 A | * 7/1998 | Furuya | 604/385.1 |

FOREIGN PATENT DOCUMENTS

| | | | |
|---|---|---|---|
| EP | 000496716 | * 7/1992 | 604/385.1 |
| FR | 002675993 | * 11/1992 | 604/385.1 |

* cited by examiner

*Primary Examiner*—John G. Weiss
*Assistant Examiner*—K. M. Reichle

(57) ABSTRACT

A diaper with a pocket including an exterior layer of a liquid impervious plastic material. An interior layer is formed of a liquid absorbing material. Separable vertical edges extend downwardly from the upper edge of the layers with an adhesive strip for securing the diaper on the child. Also provided is an intermediate layer of a liquid impervious plastic material in a generally rectangular configuration exterior of the interior layer and coupled at the periphery to the interior face of the exterior layer at the back, the intermediate layer extending horizontally for the majority of the extent of the back and extending vertically for the majority of the extent of the back thereby forming a large pocket for the receipt of baby-changing related objects. A slit is formed in the exterior layer for allowing entrance to and egress from the pocket. A strip of an adhesive on the interior surface of the exterior layer located immediately beneath the slit with a peel strip removably located thereon whereby the diaper may be rolled up and turned into a pocket and sealed for easy disposal.

1 Claim, 3 Drawing Sheets

DIAPER WITH A POCKET

BACKGROUND OF THE INVENTION

1. Field of the Invention

The present invention relates to a diaper with a pocket and more particularly pertains to conveniently storing baby-changing related objects such as baby powder, diaper cream, wet wipes and the like. The pocket also acts as a way of disposing of the diaper by way of actually rolling the diaper inside the pocket and fastening it with a releasable fastener such as tape or by a pile type fastener such as a velcro fastener.

2. Description of the Prior Art

The use of diapers of known designs and configurations is known in the prior art. More specifically, diapers of known designs and configurations heretofore devised and utilized for the purpose of forming pockets in objects through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 5,582,605 to Eric J. Lepie discloses a disposable diaper adapted to carry toiletries and sanitary accessories. U.S. Pat. No. 5,439,154 to Anna Delligatti discloses a diaper bag. U.S. Pat. No. 4,931,052 to Ruth L. Feldman discloses a diaper with integral wiping cloth and disposal container. U.S. Pat. No. 2,834,347 to A. Connally discloses a disposable diaper. U.S. Pat. No. Des. 366,315 to Blanca A. Oranday discloses a combination disposable diaper and built in wipes pocket. Lastly, PCT International Publication Number WO89/11842 to Sarbuland Khan discloses a diaper with removable absorbent pad.

While these devices fulfill their respective, particular objectives and requirements, the aforementioned patents do not describe diaper with a pocket as disclosed herein.

In this respect, the diaper with a pocket according to the present invention substantially departs from the conventional concepts and designs of the prior art, and in doing so provides an apparatus primarily developed for the purpose of conveniently storing baby-changing related objects such as baby powder, diaper cream, wet wipes and the like, as well as disposing of the soiled diaper in an odor free manner.

Therefore, it can be appreciated that there exists a continuing need for a new and improved diaper with a pocket which can be used for conveniently storing baby-changing related objects such as baby powder, diaper cream, wet wipes and the like, as well as the proper disposal of the soiled diaper. In this regard, the present invention substantially fulfills this need.

SUMMARY OF THE INVENTION

In view of the foregoing disadvantages inherent in the known types of diapers of known designs and configurations now present in the prior art, the present invention provides an improved diaper with a pocket. As such, the general purpose of the present invention, which will be described subsequently in greater detail, is to provide a new and improved diaper with a pocket and method which has all the advantages of the prior art and none of the disadvantages.

To attain this, the present invention essentially comprises a new and improved diaper with a pocket for the convenient storing of baby-changing related objects such as baby powder, diaper cream, wet wipes and the like, as well as a perfect way to dispose of a soiled diaper, roll it and toss it. The diaper has an exterior layer of a liquid impervious plastic material. The exterior layer has an interior face and an exterior face and a generally horizontal upper edge for positioning around a baby. The exterior layer also has a front and a rear and a bottom and with leg holes therethrough. The diaper also has an interior layer of a liquid absorbing material. The interior layer has an interior face and an exterior face and a generally horizontal upper edge positioned around a baby. The interior layer also has a front and a rear and a bottom and with leg holes therethrough. The diaper also has separable vertical edges extending downwardly from the upper edge to the upper extent of the leg holes with adhesive strips for securing the layers on the child. The diaper further comprises an intermediate layer of a liquid impervious plastic material in a generally rectangular configuration exterior of the interior layer and coupled at the periphery to the interior face of the exterior layer at the back. The intermediate layer extends horizontally for the majority of the extent of the back and extends vertically for the majority of the extent of the back thereby forming a large pocket for the receipt of baby-changing related objects. An elongated horizontal slit is located in the exterior layer immediately below the upper edge of the intermediate layer for allowing the placement of baby-changing related objects into and from the pocket. Lastly, the diaper has a strip of an adhesive on the interior surface of the exterior layer immediately beneath the slit with a peel strip removably located thereon whereby the diaper may be rolled up and held in a rolled into the pocket orientation in anticipation of its disposal.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved diaper with a pocket which has all of the advantages of the prior art diapers of known designs and configurations and none of the disadvantages.

It is another object of the present invention to provide a new and improved diaper with a pocket which may be easily and efficiently manufactured and marketed.

It is a further object of the present invention to provide a new and improved diaper with a pocket which is of durable and reliable constructions.

An even further object of the present invention is to provide a new and improved diaper with a pocket which is susceptible of a low cost of manufacture with regard to both materials and labor, and which accordingly is then susceptible of low prices of sale to the consuming public, thereby making such diaper with a pocket economically available to the buying public.

Even still another object of the present invention is to provide a diaper with a pocket for conveniently storing baby-changing related objects such as baby powder, diaper cream, wet wipes and the like, as well as an excellent way of disposing of a soiled diaper, roll the diaper right inside the pocket and dispose of it.

Lastly, it is an object of the present invention to provide a new and improved diaper with a pocket including an exterior layer of a liquid impervious plastic material. An interior layer is formed of a liquid absorbing material. Separable vertical edges extend downwardly from the upper edge of the layers with an adhesive strip for securing the diaper on the child. Also provided is an intermediate layer of a liquid impervious plastic material in a generally rectangular configuration exterior of the interior layer and coupled at the periphery to the interior face of the exterior layer at the back, the intermediate layer extending horizontally for the majority of the extent of the back and extending vertically for the majority of the extent of the back thereby forming a large pocket for the receipt of baby-changing related objects. A slit is formed in the exterior layer for allowing entrance to and egress from the pocket.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
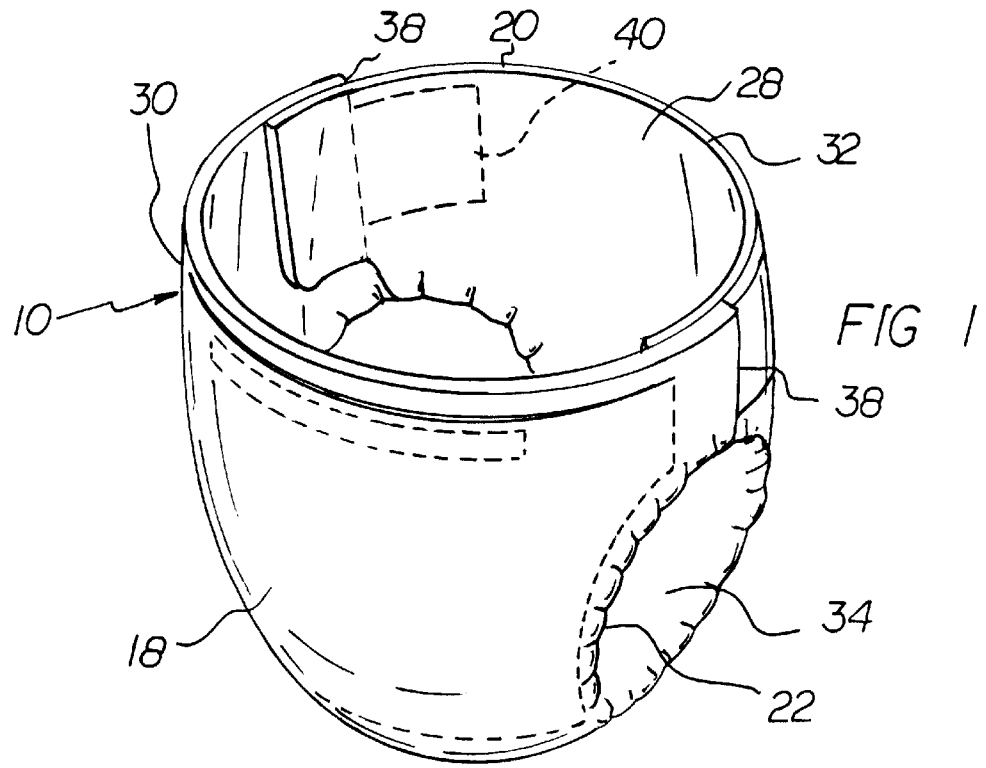
FIG. 1 is a perspective view of the preferred embodiment of the diaper with a pocket constructed in accordance with the principles of the present invention.
Figure 2:
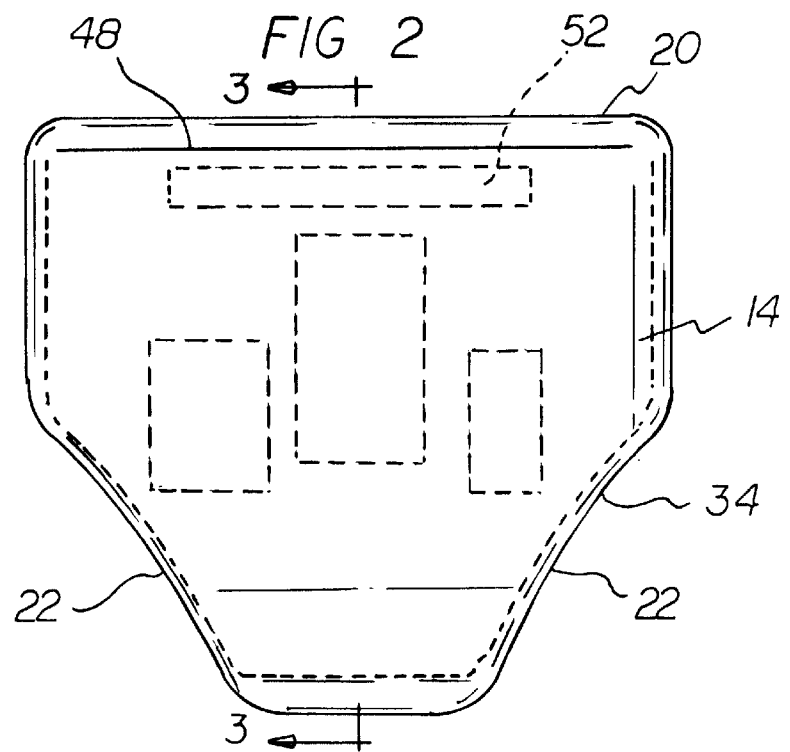
FIG. 2 is a rear elevational view of the diaper shown in FIG. 1.
Figure 3:
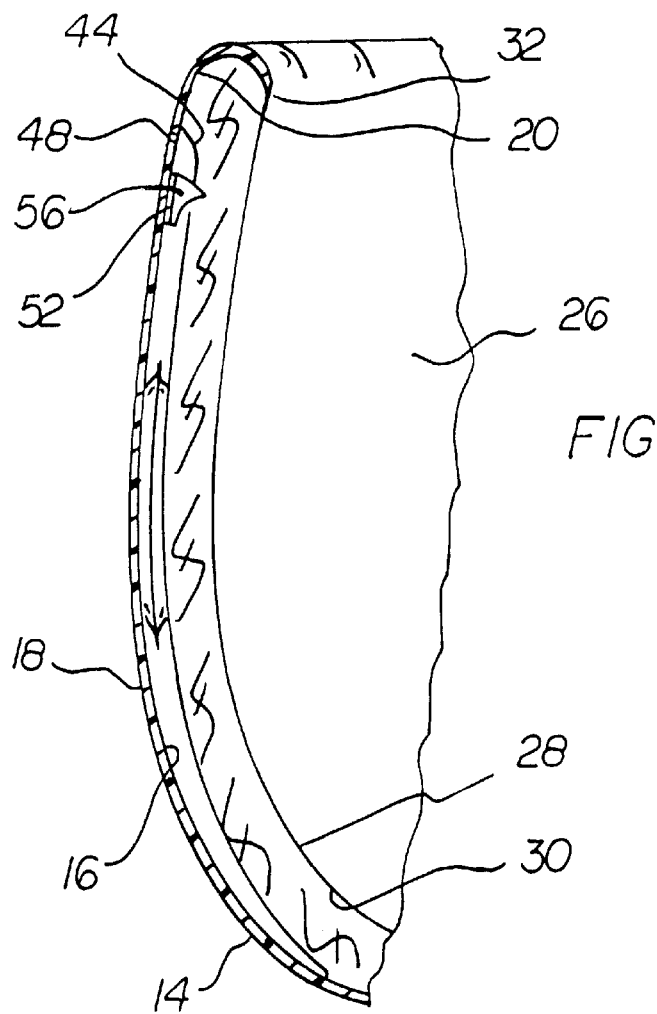
FIG. 3 is a cross-sectional view taken along line 3—3 of FIG. 2.
Figure 4:
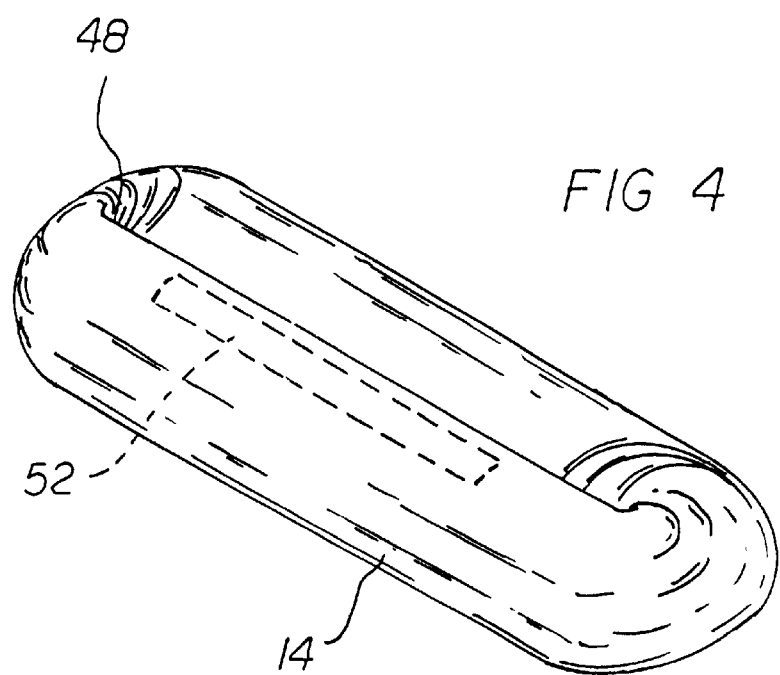
FIG. 4 is a perspective illustration of the diaper in a rolled-up configuration.
Figure 5:
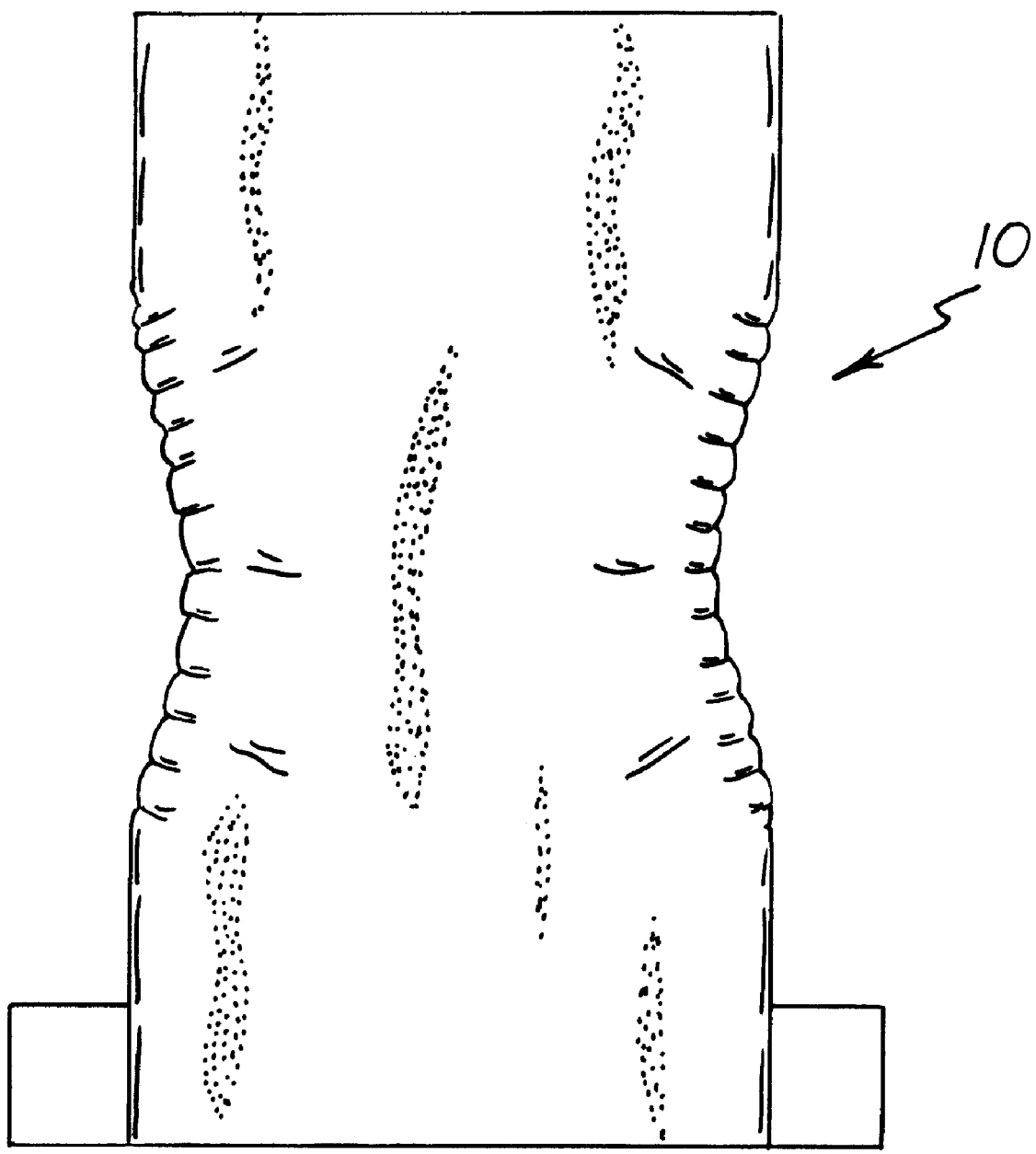
FIG. 5 is a illustration of the plain diaper without pocket or cream, powder and wipes.

With reference now to the drawings, and in particular to FIG. 1 thereof, the preferred embodiment of the diaper with a pocket embodying the principles and concepts of the present invention and generally designated by the reference numeral 10 will be described.

The present invention, the diaper with a pocket 10 is comprised of a plurality of components. Such components in their broadest context include an exterior layer, an interior layer, an intermediate layer, an adhesive strip and a slit. Such components are individually configured and correlated with respect to each other so as to attain the desired objective.

The diaper 10 with a pocket as disclosed herein is for the convenient storing of baby-changing related objects such as baby powder, diaper cream, wet wipes and the like.

The diaper has an exterior layer 14 of a liquid impervious plastic material. The exterior layer has an interior face 16 and an exterior face 18 and a generally horizontal upper edge 20 for positioning around a baby. The exterior layer also has a front and a rear and a bottom and with leg holes 22 therethrough.

The diaper also has an interior layer 26 of a liquid absorbing material. The interior layer has an interior face 28 and an exterior face 30 and a generally horizontal upper edge 32 for positioning around a baby. The interior layer also has a front and a rear and a bottom and with leg holes 34 therethrough.

The diaper also has separable vertical edges 38. Such edges extend downwardly from the upper edge to the upper extent of the leg holes. Adhesive strips 40 are provided for securing the layers on the child.

The diaper further comprises an intermediate layer 44 of a liquid impervious plastic material. Such layer is in a generally rectangular configuration. It is located exterior of the interior layer and coupled at the periphery to the interior face of the exterior layer at the back. The intermediate layer extends horizontally for the majority of the extent of the back. It also extends vertically for the majority of the extent of the back. The intermediate layer thus forms a large pocket for the receipt of baby-changing related objects.

An elongated horizontal slit 48 is located in the exterior layer. It is positioned immediately below the upper edge of the intermediate layer. It functions for allowing the placement of baby-changing related objects into and from the pocket.

Lastly, the diaper has a strip 52 of an adhesive on the interior surface of the exterior layer. Such adhesive strip is located immediately beneath the slit. In association with the adhesive strip is a peel strip 56 removably located on the adhesive strip. In this manner the diaper may be rolled up and held in a rolled up orientation in anticipation of its disposal. In place of the adhesive, there could also be utilized ZIPLOC strips or a pile-type fastener such as VELCRO fasteners.

The basic idea is a pocket or pouch on the back of the diaper. This unique idea serves two main purposes. The first purpose is the pocket's ability to hold all of the necessary toiletries for changing the child, wipes, cream and/or powder, providing an extremely convenient diaper to the consumer.

The second purpose is based on the pocket's design and use. The pocket has been situated on the diaper in a manner that allows it to be rolled and turned into the bag or pouch for easy disposal, somewhat like rolling a pair of socks. This provides the user an excellent way of disposing of the diaper, less mess, less odor.

Other options that could possibly be included are (a) to seal the bag or pocket by including a sticker strip inside the outer pocket along with the wipes, cream and/or powder; (b) a double sided ZIPLOC strip directly on the pocket would also be helpful in sealing the toiletries as well as sealing in odor and mess; and (c) VELCRO fasteners and glue could be provided as an option to seal it.

The pocket could employ elasticized sides just like the diaper itself. Manufacturing would be easy. All one has to do is lay the pocket on top of the diaper, then put it under the same machine that does the elastic part on the diaper.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the united states is as follows:

1. A diaper with a pocket adapted for the convenient storing of baby-changing related objects comprising, in combination:

an exterior layer of a liquid impervious plastic material having an interior face and an exterior face and having a generally horizontal upper edge positionable around a baby and having a front and a rear and a bottom and leg holes therethrough;

an interior layer of a liquid absorbing material having an interior face and an exterior face and having a generally horizontal upper edge positionable around the baby and having a front and a rear and a bottom and leg holes therethrough;

separable vertical edges extending downwardly from the upper edges to the upper extent of the leg holes with adhesive strips for securing the layers on the baby;

an intermediate layer of a liquid impervious plastic material in a generally rectangular configuration exterior of the interior layer and coupled at the periphery to the interior face of the exterior layer at the rear, the intermediate layer having an upper edge adjacent to the upper edge of the exterior layer and extending horizontally for the majority of the extent of the rear and extending vertically for the majority of the extent of the rear thereby forming a large pocket;

an elongated horizontal slit in the exterior layer immediately below the upper edge of the intermediate layer for allowing the placement into and removal from the pocket of baby-changing related objects; and a strip of an adhesive within the pocket on the interior surface of the exterior layer immediately beneath and parallel with the slit with a peel strip removably located thereon whereby the diaper may be rolled up and turned into the pocket and sealed for easy disposal.

* * * * *